United States Patent [19]

Jaruzelski

[11] 4,153,562

[45] May 8, 1979

[54] ANTIOXIDANTS FOR LOW ASH AND MEDIUM ASH LUBRICATING OILS

[75] Inventor: John J. Jaruzelski, Westfield, N.J.

[73] Assignee: Exxon Research & Engineering Co., Florham Park, N.J.

[21] Appl. No.: 863,793

[22] Filed: Dec. 23, 1977

[51] Int. Cl.² ............................................. C10M 1/48
[52] U.S. Cl. ............................. 252/46.6; 252/400 A; 260/137; 260/934
[58] Field of Search .............. 252/46.6, 400 A; 44/76; 260/137, 934

[56] References Cited

U.S. PATENT DOCUMENTS

| | | | |
|---|---|---|---|
| 2,226,334 | 12/1940 | Cantrell et al. | 252/46.6 X |
| 2,226,336 | 12/1940 | Cantrell et al. | 252/46.6 X |
| 2,253,228 | 8/1941 | Cantrell et al. | 252/46.6 X |
| 2,357,211 | 8/1944 | Lincoln et al. | 252/46.6 X |
| 2,619,482 | 11/1952 | Beare et al. | 252/46.6 X |
| 2,665,295 | 1/1954 | Augustine | 252/46.6 X |
| 3,135,692 | 6/1964 | Kjonaas | 252/46.6 X |
| 3,145,176 | 8/1964 | Knapp et al. | 252/46.6 X |
| 3,310,491 | 3/1967 | Jones et al. | 252/46.6 |
| 3,558,490 | 1/1971 | Lowe | 252/46.6 |

*Primary Examiner*—Delbert E. Gantz
*Assistant Examiner*—Andrew Metz
*Attorney, Agent, or Firm*—Frank T. Johmann

[57] ABSTRACT

Highly effective antioxidants that are particularly useful in crankcase lubricating oil formulations of relatively low ash content are prepared by the condensation of phosphorodithioates of alkyl phenol sulfides with compounds having activated double bonds, particularly with styrene, alkyl styrenes, highly reactive olefins, vinyl esters and acrylate esters.

16 Claims, No Drawings

ANTIOXIDANTS FOR LOW ASH AND MEDIUM ASH LUBRICATING OILS

FIELD OF THE INVENTION

This invention concerns improved antioxidants for lubricating oil compositions, and particularly for compounded lubricating oils that are intended for heavy duty use in automotive crankcases wherein the oil compositions possess high detergency, efficient sludge dispersant action and high resistance to oxidative deterioration.

The antioxidants of the invention comprise certain reaction products of alkyl phenol sulfide dithiophosphoric acid esters and unsaturated materials.

REFERENCES TO THE PRIOR ART

It is taught in the Lowe patent, U.S. Pat. No. 3,558,490, that the styryl esters of O,O-di(alkylphenyl) phosphorodithioic acid are effective antioxidant agents for hydrocarbon lubricating oils. The art is replete with teachings of the use of metal salts, particularly the zinc salts, of dialkyl dithiophosphoric acids as lubricating oil additives. Phosphorodithioate derivatives of alkyl phenol sulfides useful as lubricant additives are taught in Belgian Pat. No. 855,566.

DESCRIPTION OF THE INVENTION

In accordance with the present invention it has been found that effective antioxidants for hydrocarbon lubricating oils can be prepared by condensation of certain unsaturated materials with dithiophosphoric acids that have been obtained from alkyl phenol sulfides having from about 3 to about 20 carbon atoms in alkyl groups. The unsaturated materials that are condensed with the dithiophosphoric acids include styrene, alkylated styrene having from 1 to 6 carbon atoms in alkyl groups, highly reactive olefins of 7 to about 12 carbon atoms, vinyl esters having a total of from 4 to about 20 carbon atoms, and acrylate or methacrylate esters having a total of from 4 to about 20 carbon atoms.

The preparation of alkyl phenol sulfides is of course well known in the art and involves reaction of alkyl phenols with sulfur halides, the reaction with sulfur monochloride producing primarily an alkyl phenol disulfide and the reaction with sulfur dichloride producing primarily an alkyl phenol monosulfide.

The preparation of organic dithiophosphoric acids, more properly called diesters of dithiophosphoric acids, is also well known in the art, and most commonly involves reacting an organic compound containing a hydroxyl group, such as an alcohol or a phenol, with phosphorus pentasulfide in the ratio of four OH groups for each mole of $P_2S_5$.

Examples of the alkyl phenol sulfides useful as starting materials in the practice of this invention include those derived from amyl phenol, octyl phenol, nonyl phenol, dodecyl phenol, cetyl phenol, and octadecyl phenol. Sulfides of mixed alkyl phenols can also be employed.

The unsaturated compounds that are condensed with the alkyl phenol sulfide dithiophosphoric acid esters in preparing the antioxidant materials of this invention are characterized as having a reactive double bond. They include styrene; alkyl styrenes having up to 6 carbon atoms in alkyl groups, such as methyl styrene, ethyl styrene, and hexyl styrene; highly reactive olefins of 7 to about 12 carbon atoms; vinyl alcohol esters of from 4 to about 20 carbon atoms such as vinyl acetate, vinyl butyrate, vinyl benzoate, vinyl octoate, and vinyl stearate; and esters of acrylic acid or methacrylic acid of from 4 to 20 carbon atoms such as methyl methacrylate, ethyl acrylate, butyl methacrylate, octyl acrylate and dodecyl methacrylate. The highly reactive olefins referred to above are characterized as being other than straight chain and as having from 7 to about 12 carbon atoms. Non-limiting examples include methylene cyclohexane, propylene cyclohexane, 2,3-dimethyl 2-pentene and 2-methyl, 3-ethyl 2-hexene.

To prepare the additives of this invention it is desirable to use an excess of the alkyl phenol sulfide over the amount theoretically required to form the desired dithiophosphoric acid ester when reacting the phenol sulfide with $P_2S_5$, so as to leave up to 50% of those initially available hydroxyl groups as free OH groups in the phenol sulfide moiety of the dithiophosphoric acid ester. Thus in the reaction of the dithiophosphoric acid ester with styrene the reaction and the general structure of the product could be represented as follows:

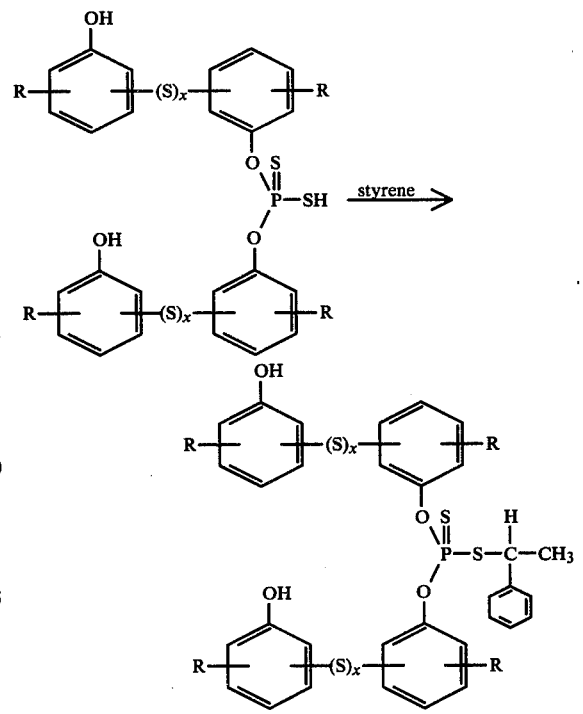

In the above formulae the symbol $—(S)_x—$ indicates that the alkyl phenol sulfide can be either the mono- or the disulfide, x being 1 or 2. The monosulfide usually includes small quantities of the disulfide. It will be seen from the above that condensation occurs at the double bond of the unsaturated material.

In the condensation of the dithiophosphate with the unsaturated compound, such as styrene, it is preferred to employ an excess, e.g. as much as 25% excess over the theoretical amount required as indicated in the reaction. The reaction is conducted at a temperature in the range of about 150° to 250° F. for from about 2 to 5 hours. The reaction is considered completed when no further reduction in total acid number (TAN) of the product is observed.

The additives of this invention can be used in concentrations ranging from about 0.001 to about 10% by weight in oil compositions ranging from gasoline through middle distillate fuels and lubricating oils. In lubricating oils the concentrations that are employed will ordinarily be within the range of about 0.1 to about 5 wt. %. Mineral lubricating oils, synthetic hydrocarbon oils, e.g. those obtained by olefin polymerization, or other synthetic oil base stocks may be used. The latter include phosphate esters, carbonate esters, halogenated hydrocarbons, polysilicones, dibasic acid esters such as di-2-ethylhexyl sebacate, polyglycols, glycol esters, complex esters, and so forth. The mineral lubricating oils can be of paraffinic base, naphthenic base or mixed base type.

In middle distillate fuels the concentration ranges will normally be from about 0.002 to about 0.2 wt. %. The fuels comprise petroleum distillates boiling within the range of about 300 to 900° F. such as diesel fuel, No. 2 fuel oil and various jet fuels. In gasoline compositions the concentrations will generally range from about 0.001 to about 1 wt. %.

Concentrates of the additives of this invention ranging from 10 to 60 wt. % of active ingredient in oil can also be prepared.

In either the fuel or lubricant compositions or in concentrates, other conventional additives may also be present, including dyes, antiwear agents, viscosity index improvers, detergents, rust preventives, dispersants and other antioxidants.

The antioxidants of the invention are particularly useful in compounded lubricants that contain detergents or dispersants of a conventional nature that can be either of the metal-containing type or of the ashless or non-metallic type, or both.

The metal-containing detergents or combination detergent-inhibitors include the alkaline earth metal salts of alkylated phenols or of alkylated phenol sulfides, as for example barium-calcium nonyl phenol sulfide, the so-called basic alkaline earth metal sulfonates, and dispersions of barium carbonate or calcium carbonate in mineral oils containing various surfactants such as phosphosulfurized polyolefins, for example.

The sulfonates are well known in the art and are the oil-soluble alkaline earth metal salts of high molecular weight sulfonic acids obtained by sulfonating either natural or synthetic hydrocarbons. Specific examples of suitable sulfonates include calcium petroleum sulfonate, barium petroleum sulfonate, calcium di-$C_9$ alkyl benzene sulfonate ($C_9$ group from tripropylene), and barium $C_{16}$ alkyl benzene sulfonate ($C_{16}$ group from tetraisobutylene). The sulfonates may be of either the neutral type or of the "over-based" or "high alkalinity" type, containing metal base in excess of that required for simple neutralization, wherein usually the excess metal base has been neutralized with carbon dioxide.

Metal salts of alkyl phenols and of the alkyl phenol sulfides (i.e., alkyl phenol thioethers) are also well known in the art. Metal salts of alkyl phenols having alkyl groups of from 5 to 20 carbon atoms are usually preferred, and the metal used to form the phenate is preferably an alkaline earth metal, e.g., calcium or barium, although other salts such as those of aluminum, cobalt, lead or tin are sometimes used. A specific example is the barium salt of the alkylation product of phenol with tripropylene. Metal salts of the corresponding alkyl phenol sulfides may also be used, e.g., barium tert.-octyl phenol sulfide.

Other detergent additives include the reaction products of phosphosulfurized hydrocarbons with alkaline earth metal oxides or hydroxides, which can be prepared by first treating a hydrocarbon with a phosphorus sulfide and then reacting the product with an alkaline earth metal hydroxide or oxide, for example barium hydroxide, preferably in the presence of an alkyl phenol or an alkyl phenol sulfide and also preferably in the presence of carbon dioxide.

Ashless detergents or dispersants include high molecular weight polymeric dispersants made with one or more polar monomers, such as vinyl acetate, vinyl pyrrolidone, methacrylates, fumarates and maleates. These dispersants have average molecular weights in the range of about 500 to 50,000. One example is a copolymer of 65 to 85 wt. % of mixed $C_9$ to $C_{12}$ fumarates, 10 to 20 wt. % of vinyl acetate, and 5 to 15 wt. % of N-vinyl pyrrolidone. Another example is the copolymer derived by reaction of mixed tallow alcohol fumarates and $C_8$ oxo alcohol fumarates, averaging about 420 molecular weight, with vinyl acetate in a 3 to 1 acetate-fumarate ratio, and 3 wt. % of maleic anhydride, followed by subsequent removal of excess vinyl acetate. By tallow alcohol fumarates is meant the esters of fumaric acid and the alcohols derived by hydrogenation of tallow. The latter are principally $C_{16}$ and $C_{18}$ aliphatic alcohols with minor amounts of $C_{12}$, $C_{14}$ and $C_{20}$ alcohols. $C_8$ oxo alcohols are prepared by reaction of carbon monoxide and hydrogen on mixed $C_3$ and $C_4$ olefins, followed by hydrogenation of the resulting aldehydes.

Particularly useful dispersants are those that contain nitrogen and that are characterized by the presence of a long hydrocarbon chain and by the possession of an acid group attached to an amino group through an imide, ester, amide or salt group. One dispersant of this type is obtained by condensation of an alkenyl succinic anhydride such as polyisobutenyl anhydride with a polyamine such as tetraethylene pentamine. See for example U.S. Pat. Nos. 3,202,678; 3,154,560; and 3,172,892. Another type is obtained by reaction of a long chain monocarboxylic acid such as polyisobutenyl propionic acid with a polyamine such as tetraethylenepentamine. See, for example, U.S. Pat. No. 3,786,077.

The nature of this invention will be further understood when reference is made to the following examples, which include a preferred embodiment, teach how the additives of the invention can be prepared, and demonstrate the superiority of the additives over similar products of the prior art.

EXAMPLE 1

A mixture of nonylphenol sulfides and dinonylphenol sulfides having a sulfur content of 7.1 wt. % was prepared by reaction of mixed nonyl and dinonyl phenols with sulfur dichloride by procedures well known in the art. The mixed alkyl phenols were prepared by alkylating phenol with tripropylene and contained about 65 to 70 wt. % of nonylphenol and about 30 to 35 wt. % of dinonylphenol.

To 400 grams of the mixed nonylphenol sulfides heated to 280° to 285° F. there was added over a period of one hour 38 grams of $P_2S_5$ with stirring. Then the reaction mixture was soaked for an additional hour at the above temperature while sparging with a stream of nitrogen. The resulting dithiophosphoric acid mixture was found to have a sulfur content of 10.4 wt. % and a phosphorus content of 2.5 wt. %.

To 375 grams of the thiophosphoric acids prepared as described, heated to 210° F., there was added over a 30-minute period 48 grams of styrene, and the temperature of the mixture was maintained at 210° F. with stirring for an additional two hours. Then the product was stripped with nitrogen at 210°-220° F. for one hour. The finished product had a viscosity of 211 SUS at 210° F. and analyzed 8.85 wt. % sulfur and 1.90 wt. % phosphorus.

EXAMPLE 2

A blend was prepared consisting of 127 grams of petroleum white oil and 300 grams of dodecyl phenol (of which 95% was monododecyl phenol) prepared by alkylating phenol with tetrapropylene. The petroleum white oil had a viscosity of 70 SUS at 100° F. and a specific gravity (60°/60° F.) of 0.845. The blend was heated to 180° F. and to it was added with agitation 104 grams of $SCl_2$ over a 30 minute period. Then the reaction mixture was heated at 180° F. for an additional 60 minutes with nitrogen sparge. The final stripped product had a hydroxyl number of 125 and analyzed 7.27 wt. % sulfur and 1.05 wt. % chlorine.

The entire reaction product obtained above was reacted with 46.5 grams of $P_2S_5$ at 285° F. in the same manner as in Example 1, soaked for an additional 2-hour period at 285° F., and then sparged with nitrogen for 15 minutes while the mixture cooled. After the thiophosphoric acid product was filtered, it analyzed 11.8 wt. % sulfur and 3.18 wt. % phosphorus.

Using the procedure described in Example 1, 300 grams of the above dithiophosphoric acid product was condensed with 44 grams of styrene. Analysis of the styrene adduct showed it to contain 10.3 wt. % sulfur, 2.63 wt. % phosphorus and 0.75 wt. % chlorine.

EXAMPLE 3

Several fully formulated high dispersancy lubricating oil formulations suitable for use in the crankcase of an internal combustion engine were prepared using the following materials in the amounts shown:

| Compound | Wt. % |
|---|---|
| Borated dispersant | 5.41 |
| Overbased magnesium sulfonate | 0.67 |
| Zinc dialkyl dithiophosphate | 1.17 |
| Dodecyl succinic acid | 0.55 |
| Ethylene glycol ester | 0.24 |
| Antioxidant | 0.3 to 1.25* |
| Mineral lubricating oil | Balance to make 100 |

*See Table I for specific amounts.

In the above formulations the borated dispersant was obtained by treating the condensation product of a polyamine and polyisobutenyl succinic anhydride with boric acid in 1:1 molar proportions. See U.S. Pat. No. 3,087,936. It was a concentrate of 49 wt. % active ingredient in a mineral lubricating oil and analyzed 1.5 wt. % nitrogen and 0.35 wt. % boron. The overbased magnesium sulfonate had a total base number of 400 and consisted of about 50 wt. % active ingredient in a mineral lubricating oil, i.e. about 28 wt. % magnesium salts of alkylated aromatic sulfonic acids of about 500 molecular weight, about 20 wt. % of magnesium carbonate and the balance diluent oil. It analyzed 9.2 wt. % magnesium. The zinc dialkyl dithiophosphate was in the form of an additive concentrate consisting of about 25 wt. % of petroleum lubricating oil and about 75 wt. % of mixed zinc dialkyl dithiophosphates prepared by treating a mixture of isobutanol and mixed amyl alcohols with $P_2S_5$ followed by treating with zinc oxide. The ethylene glycol ester was isooctyl phenoxy tetraethoxy ethanol, otherwise identified as Plexol. Both the Plexol and the dodecenyl succinic acid served as antirust agents. The mineral lubricating oil used in each of the blends was a solvent refined neutral petroleum oil having a viscosity of about 150 SUS at 100° F.

Each of the above compounded lubricating oil blends was tested for stability against oxidation by a procedure using differential scanning calorimetry. See the article by F. Noel and G. E. Cranton in Analytical Calorimetry, Vol. 3, pages 305-320 (1974) "Application of Scanning Calorimetry to Petroleum Oil Oxidation Studies". The general technique described was followed, using a temperature of 210° C. and measuring the time from the beginning of the oxidation period to the point of maximum degradation, calling this the induction time in minutes.

The results obtained in these tests are given in Table I which follows. The comparative antioxidant is of the type taught in U.S. Pat. No. 3,558,490 of Warren Lowe, referred to above, following the procedure of Example 1 but employing mixed nonylphenol rather than mixed nonylphenol sulfide to prepare the organic dithiophosphoric acid ester. The results clearly show the superiority of the antioxidant of the present invention over the prior art product. Blend 8 was tested to show the effect of not adding either type of antioxidant.

TABLE I

| Antioxidant Used Blend | Quantity Present Wt. % Based on Total Composition | | | | | | | |
|---|---|---|---|---|---|---|---|---|
|  | 1 | 2 | 3 | 4 | 5 | 6 | 7 | 8 |
| Example 1 | 0.30 | 0.50 | 0.75 | 1.25 | — | — | — | — |
| Example 2 | — | — | — | — | 0.5 | — | — | — |
| Comparative Product of Prior Art | — | — | — | — | — | 0.30 | 1.25 | — |
| Results Induction Time in Minutes | 11.0 | 13.3 | 14.4 | 18.5 | 17.5 | 5.0 | 5.0 | 4.1 |

EXAMPLE 4

Additional crankcase lubricating oil formulations were prepared using the following materials in the amounts shown:

| Compound | Wt. Percent |
|---|---|
| Borated dispersant | 4.87 |
| Overbased magnesium sulfonate | 1.07 |
| Overbased calcium alkyl phenol sulfide | 0.40 |
| Zinc dialkyl dithiophosphate | 1.17 |
| Anitioxidant | 0.15 to 1.0* |
| Mineral lubricating oil | Balance to make 100 |

*See Table II for specific amounts

In the above formulations the borated dispersant, the overbased magnesium sulfonate, the zinc dialkyl dithiophosphate and the mineral lubricating oil base were the same as those used in Example 3. The overbased calcium alkyl phenol sulfide was derived from sulfurized dodecyl phenol and had a total base number of 250. It contained 9.2 wt. % calcium.

Following the same procedure as in Example 3 these blends were also evaluated for oxidation stability by differential scanning calorimetry. The results are given in Table II which follows, and they show the superiority of the additives of this invention over the prior art additive.

TABLE II

| Antioxidant Used Blend | Quantity Present Wt. % Based on Total Composition | | | | | | | |
|---|---|---|---|---|---|---|---|---|
|  | 1 | 2 | 3 | 4 | 5 | 6 | 7* | 8 |
| Example 1 | 0.15 | 0.30 | 0.50 | 1.00 | — | — | 0.50 | — |
| Prior Art Additive | — | — | — | — | 0.30 | 1.00 | — | — |
| Test Results |  |  |  |  |  |  |  |  |
| Induction time, min. | 21.6 | 22.9 | 25.6 | 29.9 | 13.9 | 15.7 | 26.0 | 16.2 |

*This blend also contained 8 wt. percent of viscosity index improver, with correspondingly less base oil, giving a compounded lube oil of approximately SAE 10W-30 grade. Blend 8 was tested to show the effect of not adding either type of antioxidant.

In its broader aspects, this invention is of course not limited to the specific details and examples presented as those are merely illustrative of the invention, and departures therefrom may be made without departing from the principles of the invention.

What is claimed is:

1. An oil-soluble condensation reaction product, useful as an antioxidant in lubricating oil compositions, of a dithiophosphoric acid ester of an alkyl phenol sulfide defining a SH group, with an unsaturated material which reacts with said SH group to form a thioester and which is selected from the group consisting of styrene, an alkyl styrene having from 1 to 6 carbon atoms in alkyl groups, a non-straight chain olefin of from 7 to 12 carbon atoms, a vinyl alcohol ester having a total of from 4 to about 20 carbon atoms, and an acrylate ester or methacrylate ester having a total of from 4 to about 20 carbon atoms.

2. Product as defined by claim 1 wherein the unsaturated material is styrene.

3. Product as defined by claim 2, wherein the alkyl phenol sulfide comprises nonyl phenol sulfide.

4. Product as defined by claim 2, wherein the alkyl phenol sulfide comprises dodecyl phenol sulfide.

5. The method of preparing an oil-soluble additive having antioxidant properties when added to a hydrocarbon fuel, to a hydrocarbon lubricating oil or synthetic lubricating oil, which comprises reacting $P_2S_5$ with an alkyl phenol sulfide having from about 3 to about 20 carbon atoms in each alkyl group, and condensing the resulting dithiophosphoric acid ester defining a SH group, with an unsaturated compound which reacts with said SH group to form a thioester and which is selected from the group consisting of styrene, an alkyl styrene having from 1 to 6 carbon atoms in alkyl groups, a non-straight chain olefin of from 7 to about 12 carbon atoms, a vinyl alcohol ester having a total of from 4 to about 20 carbon atoms, and an acrylate ester or methacrylate ester having a total of from 4 to about 20 carbon atoms.

6. The method of claim 5 wherein in the reaction of alkyl phenol sulfide with $P_2S_5$ an excess of alkyl phenol sulfide is used over the amount theoretically required to form the desired dithiophosphoric acid so as to ensure the presence of free OH groups in the phenol sulfide moiety of the dithiophosphoric acid.

7. The method of claim 5, wherein said unsaturated compound is styrene and wherein the reaction between the dithiophosphoric acid ester and the unsaturated compound is conducted at a temperature in the range of about 150° F. to 250° F. for from about 2 to 5 hours.

8. An improved oil composition comprising an oil selected from the group consisting of a hydrocarbon fuel, a hydrocarbon lubricating oil and a synthetic lubricating oil to which has been added an oxidation inhibiting amount of said oil-soluble condensation product defined by claim 1.

9. Composition as defined by claim 8 wherein the amount of additive is from about 0.001 to about 10 wt. %, based on the total composition.

10. Product as defined by claim 1, wherein said dithiophosphoric acid ester is formed by the reaction of $P_2S_5$ with an excess of alkyl phenol mono or disulfide having about 3 to 20 carbon atoms in each alkyl group and about 1 to 2 alkyl groups per phenol moiety, and wherein about half of the initial OH groups remain unreacted in said product.

11. Product according to claim 10, wherein said unsaturated material is styrene.

12. A lubricating oil composition containing an oxidation inhibiting amount of the product of claim 2.

13. A lubricating oil composition containing an oxidation inhibiting amount of the product of claim 3.

14. A lubricating oil composition containing an oxidation inhibiting amount of the product of claim 4.

15. A lubricating oil composition containing an oxidation inhibiting amount of the product of claim 10.

16. A lubricating oil composition containing an oxidation inhibiting amount of the product of claim 11.

* * * * *